United States Patent
Wei et al.

[19]

[11] Patent Number: 5,959,733
[45] Date of Patent: Sep. 28, 1999

[54] NON-CONTACT CONTINUOUS PHOTOELECTRIC INSPECTING DEVICE FOR PAINT COATING CONTAMINATION ON WELDING SEAMS OF STEEL CAN SHEET

[75] Inventors: Shyan-Chiin Wei; Wei-Chong Tsai, both of Hsin-Chu, Taiwan

[73] Assignee: Food Industry Research and Development Institute, Hsin-ch, Taiwan

[21] Appl. No.: 09/074,846

[22] Filed: May 8, 1998

[51] Int. Cl.$^6$ ..................................................... G01B 11/30
[52] U.S. Cl. ........................................ 356/371; 356/237.1
[58] Field of Search ........................... 356/237, 445–448, 356/371, 394, 375, 376, 429–431, 239, 338; 219/130.01, 124.34, 130.21; 340/825.16, 825.17

[56] References Cited

U.S. PATENT DOCUMENTS

| | | | |
|---|---|---|---|
| 4,988,201 | 1/1991 | Sugitani et al. | 356/376 |
| 5,442,155 | 8/1995 | Nihei et al. | 219/130.01 |
| 5,481,085 | 1/1996 | Kovacevic et al. | 219/130.01 |
| 5,596,412 | 1/1997 | Lex | 356/371 |
| 5,644,141 | 7/1997 | Hooker et al. | 356/376 |

Primary Examiner—Hoa Q. Pham
Attorney, Agent, or Firm—Merchant & Gould P.C.

[57] ABSTRACT

This invention relates to a non-contact continuous photoelectric inspecting device for paint coating contamination on welding seams of steel can sheet. The device uses a continuous light beam with adjustable, controllable projected light quantity as a light source, where a light beam is projected on welding seams of a steel can sheet to be inspected through a set of focusing lens that may adjust size of the light beam. Another set of light collecting lens for collecting light beam being reflected by the welding seams of the steel can sheet is provided at where the reflected light projects, wherein the reflected light beam is condensed onto a photo sensor. A set of a specially designed photoelectric converting identifying circuit controls operation of the entire inspecting device, where a set of photoelectric current amplifier converts and amplifies photoelectric currents being output by the photo sensor to voltage signals. A set of high pass filter and a clamping amplifier then eliminate low frequency interference signals and clamp high frequency signals to ground voltage. Finally, a set of single-beat output level identifier is featured with capability of identifying paint coating contamination whereby steel can sheet having a welding seam being contaminated by paint films and paint specks is immediately inspected and rejected on-line so as to effectively prevent contaminated steel can sheet from entering a welding machine, that will eventually cause machine break down.

13 Claims, 5 Drawing Sheets

NON-CONTACT CONTINUOUS PHOTOELECTRIC INSPECTING DEVICE FOR PAINT COATING CONTAMINATION ON WELDING SEAMS OF STEEL CAN SHEET

FIELD OF INVENTION

This invention relates to a non-contact inspecting device for paint coating contamination on welding seams of steel can sheet, in particular, to a non-contact inspecting device for paint coating contamination on welding seams of steel can sheet that uses a continuous light beam as a light source.

BACKGROUND OF INVENTION

Welding machines are commonly implemented in food can industry for welding can bodies nowadays. In such a welding process, steel sheet is first coated with paint and then carved; the steel sheet then enters a welding machine for welding operation. Once entering the welding machine, carved steel sheet is rolled up to form a cylindrical configuration, and an overlap of 0.3–0.5 mm is formed bet opposing edges of the cylinder body. A welding wheel conductor then welds the overlap along a cope conductor. Paint is finally added to the welded path to complete manufacturing of the steel can. It is thus known that sufficient welding seams for later welding operation must be retained during the coating operation and the welding seams should be kept away from paint contamination, because welding seams being contaminated by paint (either reulted from paint splashes that appear during coating operation or from carving error) will cause notable increment of contact resistance during welding operation and thus cause notable increment of current in the welding machine and anomalous welding teperature. Contaminated seams may also cause jump sparks and poor welding quality, fracture of copper conductor, or break down of welding machine, which all eventually interrupt production line and reduce production capability. Therefore, preventing unqualified steel sheet being contaminated by paint from entering the welding line can help to avoid such damages. An automatic inspecting system is usually provided at entrace of the welding line. Unqualified parts are automatically rejected when the system detects that a welding seam of the steel sheet is contaminated by paint. Such a measure may not only lower defective rate, but also help to prevent from damaging the machine.

Currently, a resistance inspecting device for paint coating continuation on welding seams of steel can sheet is commonly used for inspection purpose. In such a device, a contact inspecting device is provided on the steel sheet carving machine. The inspecting device primarily uses the wheel conductor to measure resistance of welding seams of the steel sheet, where measured resistance values are used as a basis for selecting quaified parts. However, accuracy of such a contact inspecting method is eventually reduced due to contamination of the contact surface after prolong operation.

In view of the above disadvantage of conventional contact resistance inspecting device for paint coating contamination on welding seams of steel can sheet, this invention provides a non-contact continuous photoeletric inspecting device for paint coating contamination on welding seams of steel can sheet. Because the inspecting device of this invention can effectively regulate specifications and quality of incoming material, it greatly enhances competitiveness of metal cans in packaging industry.

BRIEF DESCRIPTION OF INVENTION

It is a primary object of this invention to provide a non-contact continuous photoelectric inspeting device for paint coating contamination on welding seams of steel can sheet, the inspecting device comprising: a continuous light source, a focusing lens, a collecting lens, a photo sensor, a pre-amplifier, a high pass filter, a low pass filter amplifier, a level detector, an alarming indicator, and an output interface. The inspecting device primarily implements a continuous light beam, which is projected on the steel can sheet through the focusing lens. Reflected and scatterd light signals are transmitted through the collecting lens into the photo sensor and the pre-amplifier. The pre-amplifier converts photoelectric currverts to voltage signals output. The high/low pass filter amplifier then eliminate unnecessary interference signals. The voltage signals are then fed into an identifying circuit of the level detector so as to detect whether a steel can sheet enters a detection zone and to identify whether the steel can sheet entering the detection zone is contaminated by paint coating. In case paint coating contamination is detected, the alarming indicator is turn on and furnishes signals to the output interface. The output interface transmits the signals to an externally connected rejection actuator upon receipt of the signals and rejects a defective part.

It is another object of this invention to provide a non-contact continuous photoelectric inspecting device for paint coating contamination on welding seams of steel can sheet, where the inspecting device is featured with excellent capability of inspecting surface flaws and prompt inspecting response.

It is a further object of this invention to provide a non-contact continuous photoectric inspecting device for paint coating contamination on welding seams of steel can sheet, where the inspecting device conducts 100% inspection on paint coating contamination status of the welding seams of steel can sheet; inspecting precision may be further enhanced by adjusting, diameter of the light beam, gain of the pre-amplifier, sensitivity of the level detector, and power of light beam.

It is a further object of this invention to provide a non-contact continuous photoelectric inspecting device for paint coating contamination on welding seams of steel can sheet, where inplementation of the inspecting device efectively enhances production capability and quality of metal can packaging and greatly enhances competiveness of metal cans in packaging industry.

DETAILED DESCRIPTION OF INVENTION

Figure 1A:
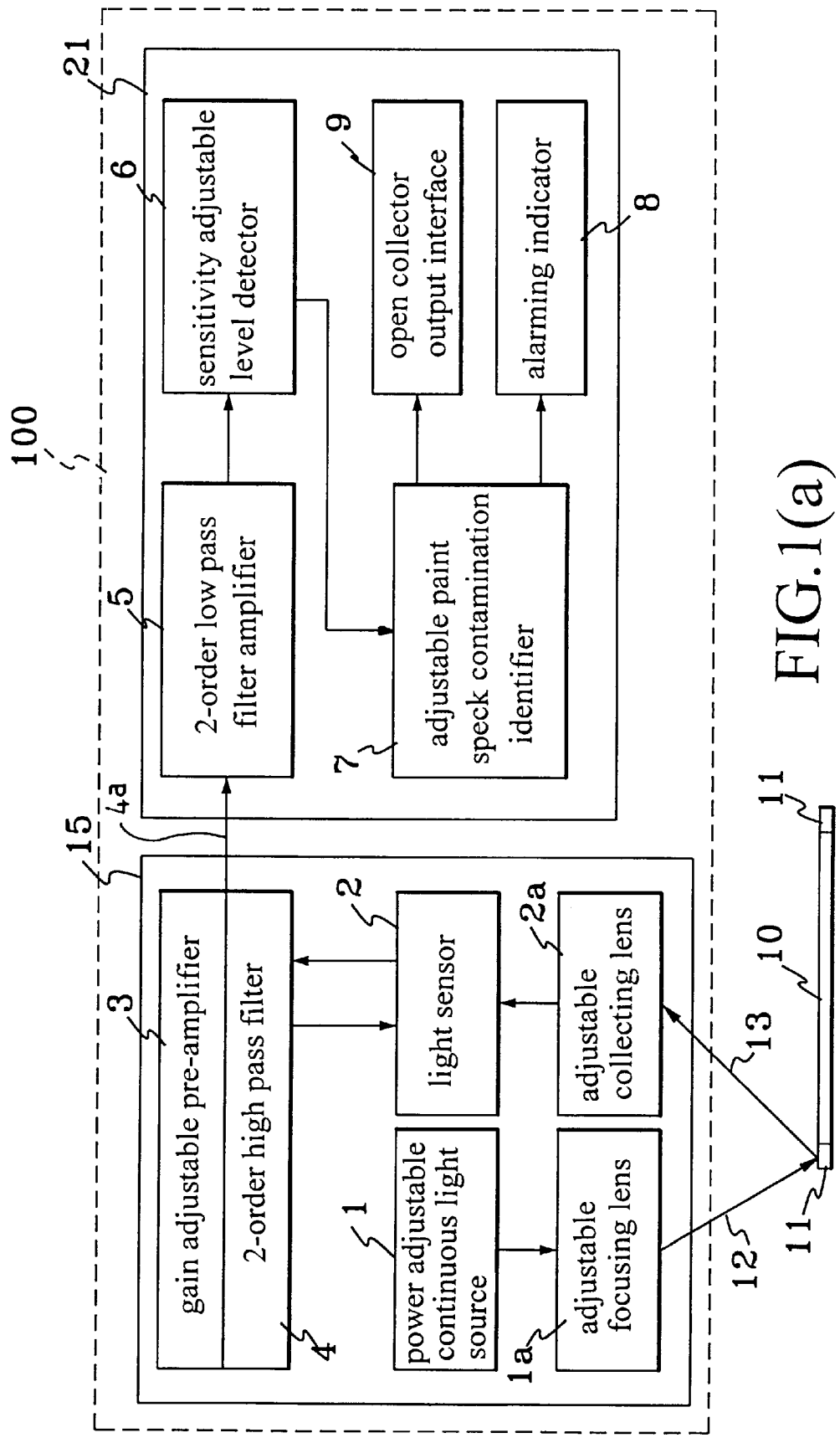
FIG. 1(a) is a block diagram illustrating internal functions of a model of a non-contact continuous photoelectric inspecting device for paint coating contamination on welding seams of steel can sheet of this invention.

FIG. 1(a) is a block diagram illustrating internal functions of a model of a non-contact continuous photoelectric inspecting device for paint coating contamination on welding seams of steel can sheet of this invention. The non-contact continuous photoelectric inspecting device 100 comprises a photoeletric inspecting head 15 and in inspecting unit 21 that are connected by a signal and power wire 4a. The photoelectric inspecting head 15 comprises a power adjustable continuous light source 1, an adjustable focusing lens 1a, a photo sensor 2, an adjustable collecting lens 2a, a gain adjustable pre-amplifier 3, and a 2-order high pass filter 4. The inspecting unit 21 comprises a 2-order low pass filter amplifier 5, an sensitivity adjustable level detector 6, an adjustable paint speck contamination identifier 7, an alarming indicator 8, and an output interface 9.

Functions and operations of above-desrcibed components are described as follows. First, the inspecting head 15 uses a light beam 12 as the light source. The light beam is projected from the power adjustable light source 1 on a welding seam 11 of a steel can sheet 10 to be inspected through the adjustable focusing lens 1a that may adjust size of the light beam. Reflected and scattered light signals 13 are collected by the adjustable collecting lens 2a, inspected by the photo sensor 2, and fed into the gain adjustable pre-amplifier 3. The pre-amplifier 3 then converts and amplifies photoelectric current signals to voltage signals output. The 2-order high pass filter 4 and the 2-order low pass filter amplifier 5 then eliminate low frequncy interference signals and clamp high frequency signals to ground voltage. Implementation of such an analog signal processing technique is primarily intended to eliminate interference signals. Voltage signals which interference signals have been eliminated are fed into an identifying circuit of the sensitivity adjustable level detector 6 to detect whether a steel can sheet enters a detect zone. Output of the level detector 6 serves as a trigger of the adjustable paint speck contamination identifier 7. In case the steel can sheet is found to be contaminated by paint coating, signals are fed into the alarming indicator 8 and the output interface 9 simultaneously. The output interface 9 transmits the signals to an externally connected rejection actuator upon receipt of the signals so as to reject the defective part.

Figure 1B:
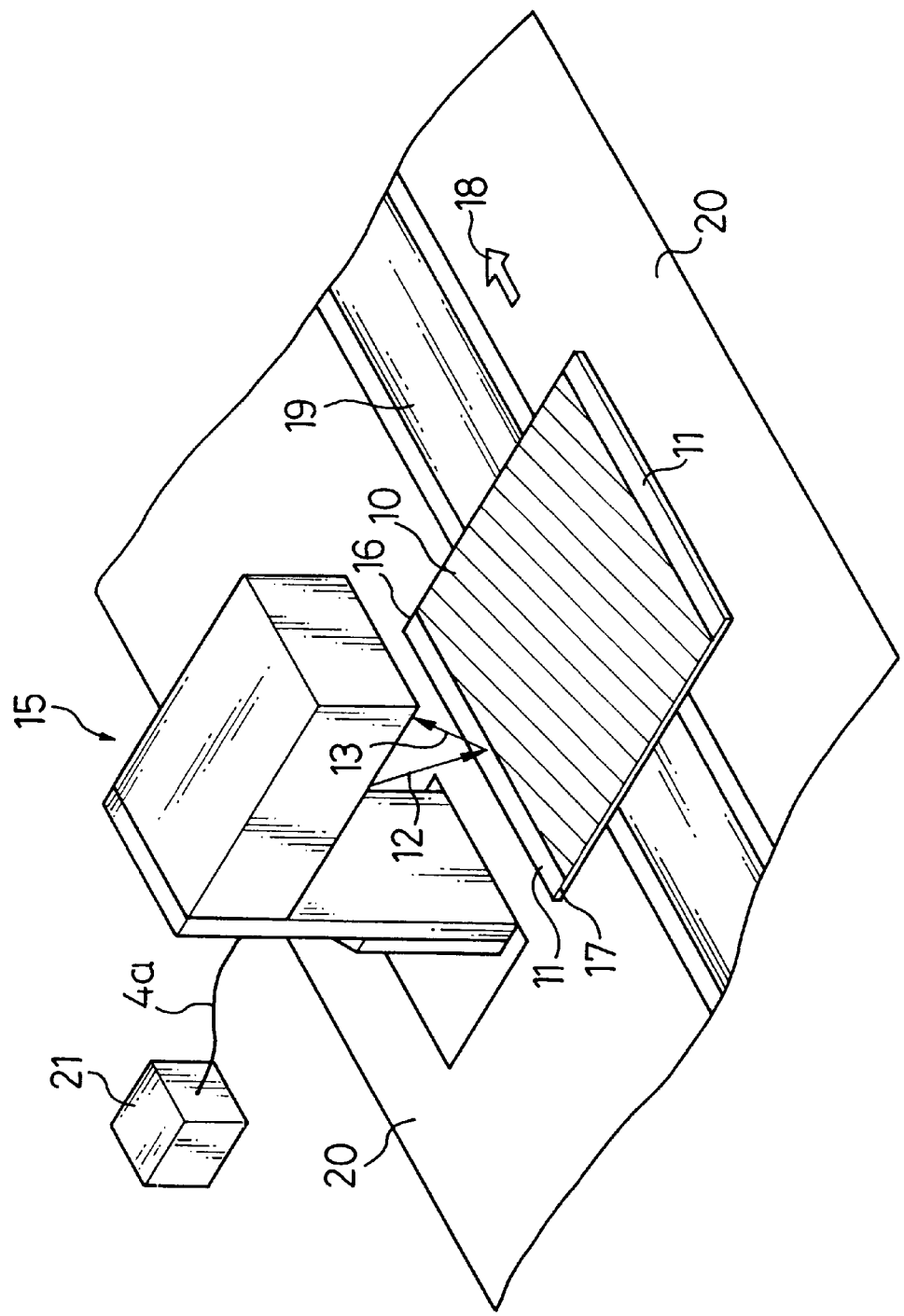
FIG. 1(b) is a perspective view illustrating dynamic arrangement of a non-contact continuous photoelectric inspecting device for paint coating contamination on welding seams of steel can sheet of this invention performing on-line inspection of paint coating contamination on welding seams.

FIG. 1(b) is a perspective view illustrating dynamic arrangement of the non-contact continuous photoelectric inspecting device 100 for paint coating contamination on welding seams of steel can sheet of FIG. 1(a) performing on-line inspection of paint coating contamination on welding seams. After the steel can sheet 10 is coated by paint and carved (where the welding seams are not coated with paint), the steel can sheet is secured on a production line conveying belt 19 (where arrow 18 indicates linear direction that the conveying belt travels, and the speed of the protection line $V=\pi DN/60$ (cm/sec), wherein$\pi$=constant=3.14159, D=diameter of belt wheel=14 cm, and N=number that the belt wheel revolves per minute=1800). The linear speed that the steel can sheet travels is approximately 1320 cm/sec. The photoelectric inspecting head 15 is installed on a machine bed 20 and is connected to the inspecting unit 21 via a signal and power wire 4a. The light source (preferably a laser light source) is turned on to calibrate position of the welding seam 11 of the steel can sheet to be inspected. At this moment, analog signals of the inspecting head 15 are coupled to the inspecting unit 21 and position calibration may be conducted in accordance with signals shown on a scope. Non-contact inspection of paint coating contamination on the welding seams 11 of the steel can sheet is ready upon completion of positioning process. In inspection operation, the light beam 12 is projected on one of the welding seams 11 of the steel can sheet (where the light beam scans from a front end 16 to a rear end 17 of the welding seam 11). The reflected and scattered light signals 13 are inspected by the photo sensor within the inspecting head 15. Photoelectric currents are then converted to voltage signals by the pre-amplifier. After eliminating interfernce signals, the voltage signals are then detected by an identifying circuit of the level detector to identify whether a steel can sheet enters the detection zone. Output of the identifying circuit of the level detector serves as a triger of the paint speck contamination identifier so as to assure that the alarming indicator outputs signals only when a steel can sheet entering the detection zone is inspected to contain a welding seam being contaminated by paint coating.

Figure 2B:
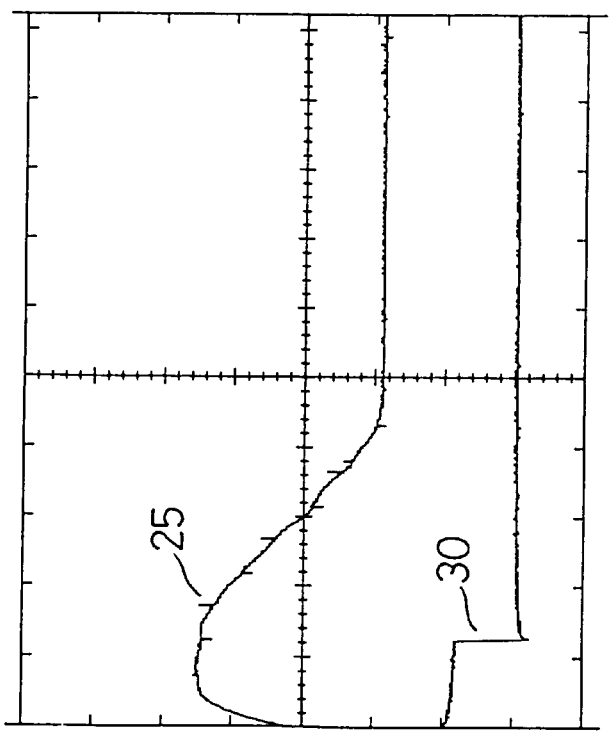
FIGS. 2(a) to 2(f) are signal graphs of paint specks and paint contamination being inspected by a non-contact continuous photoelectric inspecting device for paint coating contamination on welding seams of steel can sheet of this invention.
Figure 2A:
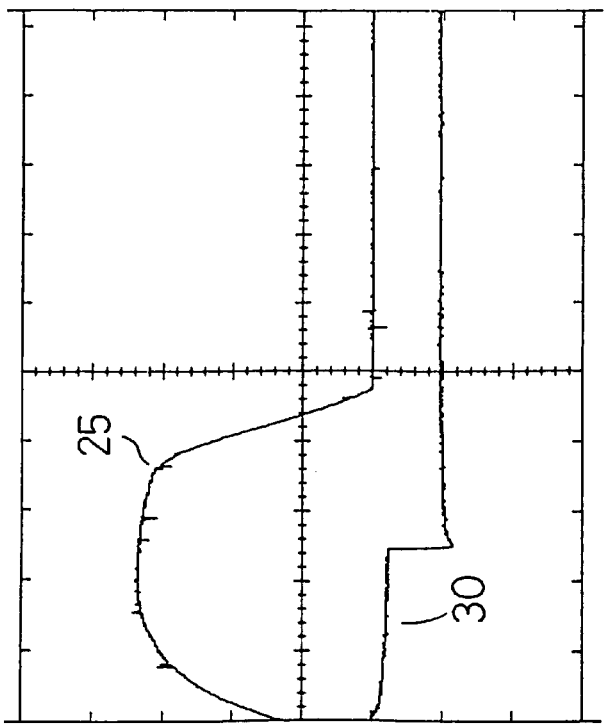
Figure 2D:
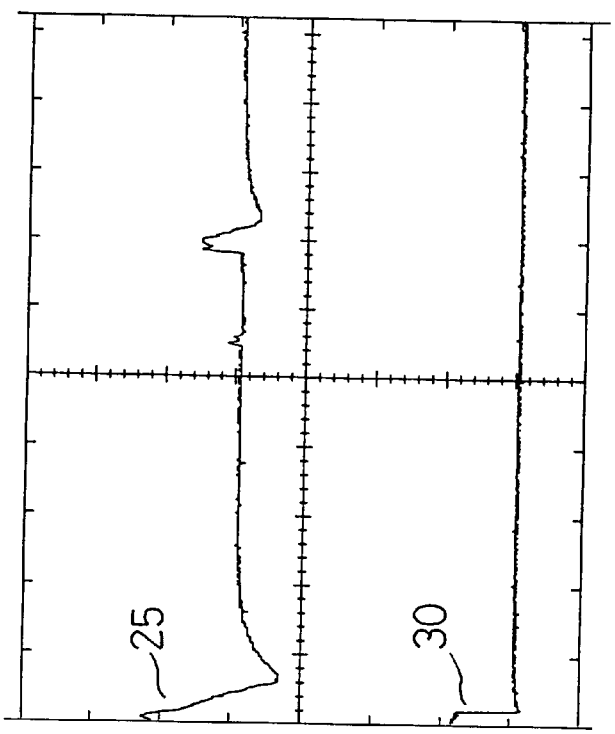
Figure 2C:
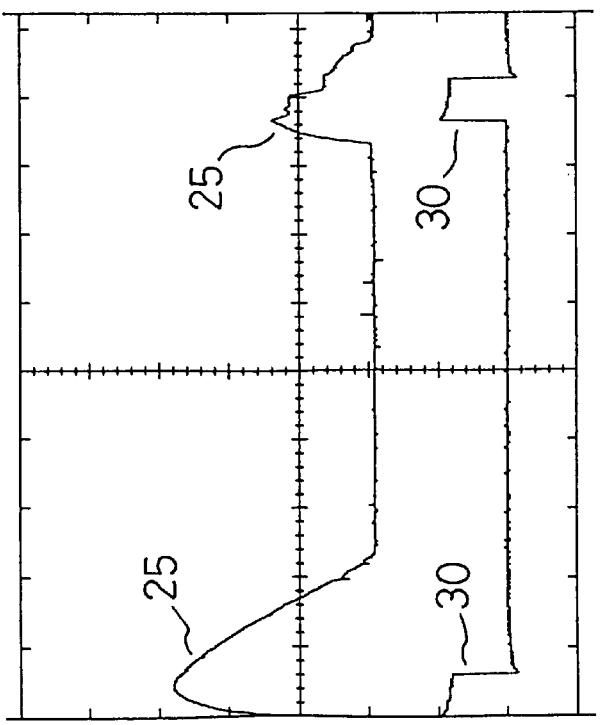
Figures 2E, 2F:
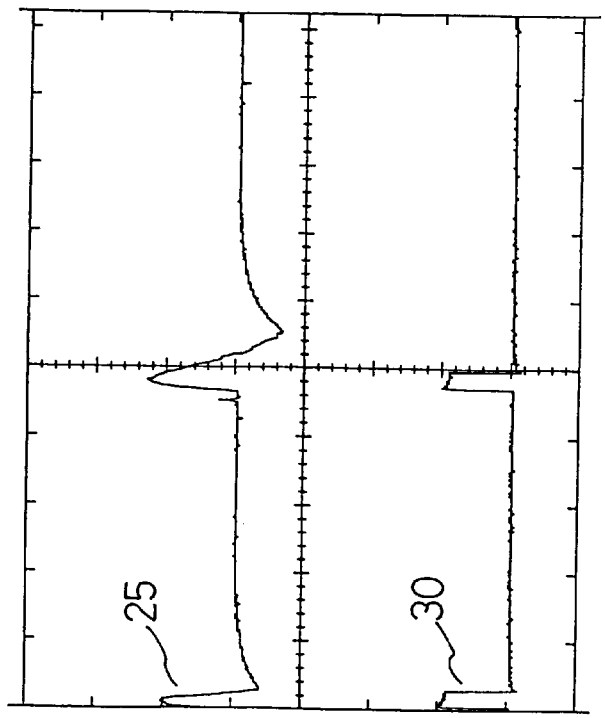

FIGS. 2(a) to 2(f) are signal graphs of paint specks and paint contamination being inspected by a non-contact continuous photoelectric inspecting device for paint coating contamination on welding seams of steel can sheet of this invention. FIGS. 2(a) and 2(b) illustrate at speck signals 25 and paint speck inspection signals 30 of welding seams being contaminated by gold paint specks. FIG. 2(a) relates to a BASF gold paint speck of approximately 2 mm in diameter; FIG. 2(b) relates to an ICI58079 gold paint speck of approximately 3.5 mm in diameter. FIGS. 2(c) and 2(d) illustrate paint speck signals 25 and pant inspection signals 30 of welding seams being contaminated by transparent paint specks. FIG. 2(c) relates to C2202 transparent paint specks of approximately 3.4/2.1 mm in diameter, FIG. 2(d) relates to an F05NT transparent paint speck of approximately 2.3 mm m immense FIG. 2(e) illiterates a paint speck signal 25 and a paint speck inspection signal 30 of a welding seam being contaminated by a white paint speck, wherein the paint speck is a 1S775H paint speck of approximately 2.5 mm in diameter. FIG. 2(f) illustrates a paint speck signal 25 and a paint speck inspection signal 30 of a welding seam being contaminated by a blue strip of 55 mm in length.

Using the non-contact continuous photoelectric inspecting device for paint coating contamination on welding seams of steel can sheet as described above can conduct 100% inspection on paint coating contamination status of the welding seams in motion without possibility of omission during inspection. Furthermore, size of light beam, power of light beam, sensitvity of inspection, and angel of inspection can all be adjusted so as to meet required sensitivity and precision. In addition, the non-contact continuous photoeletric inspecting device for paint coating contamination on welding seams of steel can sheet of this invention that using photoelectric inspecting system provides excellent capability of inspecting surface flaws and prompt inspecting response and thus guarantees inspection reliability.

What is claimed is:

1. A non-contact continuous photoeleictric inspecting device for paint coating contamination on welding seams of steel can sheet, comprising:
   a power adjustable continuous light source;
   an adjustable focusing lens;
   an adjustable collecting lens;
   a photo sensor for inspecting reflected and scattered light signals of the contiuous light source;
   a gain adjustable pre-amplifier for converting photoelectric currents being fed into the photo sensor to voltage signals;
   a set of bandpass filter for eliminating interfernce signals in accompany of the fed voltage signals from the pre-amplifier;
   a level detector for identifying whether a steel can sheet enters a detecting zone;

a contamination identifier for inspecting whether the steel can sheet is contaminated;

an alarming indicator for receiving signals of the contamination identifier and transmitting alarms of paint coating contamination; and an output interface for receiving signals generated by the contamination identifier and being externally connected to a rejection actuator which rejects a defective part.

2. The non-contact continuous photoelectric inspecting device for paint coating contamination on welding seams of steel can sheet as set forth in claim 1, wherein the inspecting device does not contact with surfaces of detected steel can sheet directly.

3. The non-contact continuous photoelectric inspecting device for paint coating contamination on welding seams of steel can sheets as set for in claim 1, wherein the continuous light source projects on surfaces of steel can sheets to be inspected, and the reflected and scattered light signals are received by the photo sensor.

4. The non-contact continuous photoelectric inspecting device for paint coating contamination on welding seams of steel can sheets as set forth in claim 1, wherein the continuous light source includes an adjustable, controllable projected light quantity, wherein the light is in the ultraviolet, visible or infra-red frequency range.

5. The non-contact continuous photoeletric inspecting device for paint coating contamination on welding seams of steel can sheet as set forth in claim 1, wherein the continuous light source is a continuous laser light source.

6. The non-contact continuous photoeletric inspecting device for paint coating contamination on welding seams of steel can sheet as set forth in claim 1, wherein size of light beam projected on surfaces of steel can sheets is adjustable.

7. The non-contact continuous photoelectric inspecting device for paint coating contamination on welding seams of steel can sheet as set forth in claim 1, wherein the photo sensor is any component featuring with light detecting function.

8. The non-contact continuous photoelectric inspecting device for paint coating contamination on welding seams of steel can sheet as set forth in claim 1, wherein the bandpass filter comprises a high pass filter circuit and a low pass filter amplifying circuit.

9. The non-contact continuous photoelectric inspecting device for paint coating contamination on welding seams of steel can sheet as set forth in claim 8, wherein the high pass filter circuit and the low pass filter amplifying circuit eliminate the low frequency interference signals and clamp high frequency signals to ground voltage.

10. The non-contact continuous photoeletric inspecting device for paint coating contamination on welding seams of steel can sheet as set forth in claim 1, wherein output of the level detector serves as a trigger of the contamination identifier.

11. The non-contact continuous photoeletric inspecting device for paint coating contamination on welding seams of steel can sheet as set forth in claim 1, wherein alarming signals are generated only when the contamination identifier detects paint contamination.

12. The non-contact continuous photoeletric inspecting device for paint coating contamination on welding seams of steel can sheet as set forth in claim 1, wherein the device conducts 100% inspection on paint coating contamination status of the welding seams in motion.

13. The non-contact continuous photoeletric inspecting device for paint coating contamination on welding seams of steel can sheet, comprising a photoelectric inspecting head and an inspecting unit connected by a signal and power wire, wherein:

the photoelectric inspection head comprises: a power adjustable continuous light source; an adjustable collecting lens; an adjustable focusing lens; a photo sensor for inspecting reflected and scatttered light signals of the continuous light source; a gain adjustable pre-amplifier for converting photoelectric currents being fed into the photo sensor to voltage signals; and a 2-order high pass filter for eliminating interference signals in accompany of the fed voltage signals from the pre-amplifier; and the inspecting unit comprises: a 2-order low pass filter amplifier for clamping the voltage signals to ground voltage; an adjustable level detector for identifying whether a steel can sheet enters a detecting zone; an adjustable contamination identifier for inspecting weather the steel can sheet is contaminated; an alarming indicator for receiving signals of the contamination identifier and transmitting alarms of paint coating contamination; and an output interface for receiving signals generated by the contamination identifier and being externally connected to a rejection actuator which rejects a defective part.

* * * * *